United States Patent
Plos et al.

(10) Patent No.: US 6,599,328 B1
(45) Date of Patent: Jul. 29, 2003

(54) COMPOSITION FOR THE OXIDATION DYEING OF KERATIN FIBERS AND DYEING PROCESS USING THIS COMPOSITION

(75) Inventors: Gregory Plos, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/593,863

(22) Filed: Jun. 15, 2000

(30) Foreign Application Priority Data

Jun. 21, 1999 (FR) .............................. 99 07828

(51) Int. Cl.$^7$ ................................. A61K 7/13
(52) U.S. Cl. ................ 8/405; 8/406; 8/407; 8/409; 8/410; 8/411; 424/70.17
(58) Field of Search ................ 8/405, 406, 401, 8/407, 409, 410, 411; 424/70.17

(56) References Cited

U.S. PATENT DOCUMENTS

| | | | |
|---|---|---|---|
| 3,251,742 A | 5/1966 | Soloway | 167/88 |
| 4,003,699 A | 1/1977 | Rose et al. | 8/10.2 |
| 4,823,985 A | 4/1989 | Grollier et al. | 222/1 |
| 5,061,289 A | 10/1991 | Clausen et al. | 8/405 |
| 5,380,340 A | 1/1995 | Neunhoeffer et al. | 8/409 |
| 5,534,267 A | 7/1996 | Neunhoeffer et al. | 424/701 |
| 5,538,517 A * | 7/1996 | Samain et al. | 8/401 |
| 5,571,458 A * | 11/1996 | Beauquey et al. | 424/70.1 |
| 5,663,366 A | 9/1997 | Neunhoeffer et al. | 548/371.4 |
| 5,766,576 A | 6/1998 | Löwe et al. | 424/62 |
| 5,769,903 A * | 6/1998 | Audousset et al. | 8/409 |
| 5,899,212 A * | 5/1999 | Sorenson et al. | 8/401 |
| 5,976,517 A * | 11/1999 | Dubief et al. | 424/70.1 |
| 6,004,355 A * | 12/1999 | Dias et al. | 8/6 |

FOREIGN PATENT DOCUMENTS

| | | | | |
|---|---|---|---|---|
| WO | WO 97/12596 | * | 4/1997 | A61K/7/48 |
| WO | WO 99/17732 | * | 4/1999 | A61K/7/13 |

* cited by examiner

*Primary Examiner*—Mark Kopec
*Assistant Examiner*—Eisa Elhilo
(74) *Attorney, Agent, or Firm*—Finnegan, Henderson, Farabow, Garrett & Dunner, L.L.P.

(57) ABSTRACT

A ready-to-use composition for the oxidation dyeing of keratin fibers, and, in particular, human keratin fibers, such as the hair, having at least one oxidation dye, at least one oxidoreductase enzyme, and at least one specific salified or chemically modified chitosan, as well as to the oxidation dyeing process using this composition.

42 Claims, No Drawings

COMPOSITION FOR THE OXIDATION DYEING OF KERATIN FIBERS AND DYEING PROCESS USING THIS COMPOSITION

The invention relates to a ready-to-use composition for the oxidation dyeing of keratin fibers, and, in particular, human keratin fibers, such as the hair, comprising, in a medium suitable for dyeing, at least one oxidation dye, at least one enzyme of 2-electron or 4-electron oxidoreductase type, and at least one specific salified or chemically modified chitosan, as well as to the dyeing process using this composition.

It is known to dye keratin fibers, and, in particular, human hair, with dye compositions containing oxidation dye precursors, in particular, ortho- or para-phenylenediamines, ortho-, or para-aminophenols, and heterocyclic bases, generally known as oxidation bases. The oxidation dye precursors, or oxidation bases, are colorless or weakly colored compounds that, when combined with oxidizing products, can give rise to colored compounds and dyes by a process of oxidating condensation.

It is also known that the shades obtained with these oxidation bases can be varied by combining them with couplers or coloration modifiers, the latter being chosen, in particular, from aromatic meta-diamines, meta-aminophenols, meta-diphenols and certain heterocyclic compounds.

The variety of molecules used as oxidation bases and couplers allows a wide range of colors to be obtained.

The so-called "permanent" coloration obtained by means of these oxidation dyes should moreover satisfy a certain number of requirements, including having no toxicological drawbacks, allowing shades to be obtained in the desired intensity and having good staying power with respect to external agents, e.g., light, bad weather, washing, permanent-waving, perspiration or rubbing.

The dyes should also allow gray hair to be covered and, finally, they should be as unselective as possible, i.e., they should allow only the smallest possible differences in coloration along the same keratin fiber, that may indeed be differently sensitized, i.e., damaged, between its tip and its root.

The oxidation dyeing of keratin fibers is generally carried out in alkaline medium, in the presence of hydrogen peroxide. However, the use of alkaline media in the presence of hydrogen peroxide can have the drawback of resulting in substantial degradation of the fibers, as well as appreciable decolorization of the keratin fibers, which is not always desirable.

The oxidation dyeing of keratin fibers can also be carried out using oxidizing systems other than hydrogen peroxide, such as enzymatic systems. Thus, it has already been proposed to dye keratin fibers, in particular, in European patent application EP-A-0 310 675, the disclosure of which is incorporated herein by reference, with compositions comprising an oxidation base and optionally a coupler, in combination with enzymes of the 2-electron oxidoreductase type, such as pyranose oxidase, glucose oxidase or uricase, in the presence of a donor for the enzymes.

It has also already been proposed, in particular, in French patent applications FR-A-2 112 549, FR-A-2 694 018, European patent application EP-A-504 005, International patent applications WO 95/07988, WO 95/33836, WO 95/33837, WO 96/00290, WO 97/19998, WO 97/19999 and U.S. Pat. No. 3,251,742, the disclosures of each of which are incorporated herein by reference, to dye keratin fibers with compositions comprising, in particular, an oxidation dye precursor and an enzyme of laccase type (4-electron oxidoreductase).

Although these dyeing processes are carried out under conditions that do not result in a degradation of the keratin fibers comparable to that generated by the dyes used in the presence of hydrogen peroxide, they lead to colorations not entirely satisfactory, especially regarding their intensity, since it is assumed that the thickeners generally used in this type of dyeing with enzymes halts the rise of the color on the fiber. In addition, molecular oxygen dissolves poorly in the conventional supports for dyeing with the enzymes, the effect of which is to reduce the hair-dyeing activity of the enzymes.

The inventors have discovered that it is possible to obtain novel dyes capable of giving more intensive colorations, by combining at least one oxidation dye, at least one enzyme of 2-electron or 4-electron oxidoreductase type, and at least one specific, salified or chemically modified chitosan.

It is also possible to obtain better conservation of the activity of the enzymes used in hair dyeing.

These discoveries form the basis of the present invention.

A first subject of the invention is thus a ready-to-use composition for the oxidation dyeing of keratin fibers, and, in particular, of human keratin fibers, such as the hair, comprising, in a medium suitable for dyeing:

at least one oxidation dye, at least one enzyme of 2-electron or 4-electron oxidoreductase type, and at least one chitosan salified with an organic or inorganic acid, allowing a visually clear solution to be obtained at a concentration of 1% in water, or a chemically modified chitosan comprising one or more units of formula (I) below:

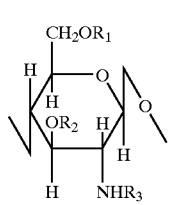

(I)

in which, $R_1$ and $R_2$, which are identical or different, are chosen from a hydrogen atom and a radical —XCOOM, $R_3$ is chosen from a hydrogen atom, a —COCH$_3$ radical and a radical —CO—X—COOM, X is chosen from a $C_1$–$C_8$ alkylene radical, optionally branched, or substituted with one or more hydroxyl, halogen or epoxy groups, M is chosen from a hydrogen atom and a cation chosen from alkali metals, alkaline-earth metals, ammonium, an organic amine and an organic alkanolamine, with the proviso that at least one of the units of formula (I) comprising a radical $R_1$ and/or $R_2$ and/or $R_3$ denotes —XCOOM and/or a radical $R_3$ denotes —CO—X—COOM.

A subject of the invention is also a process for the oxidation dyeing of keratin fibers using this ready-to-use dye composition.

The salified chitosans used in the ready-to-use dye composition according to the invention can be chosen, in particular, from those salified with an organic acid such as, for example, lactic acid, glutamic acid and, preferably, pyrrolidonecarboxylic acid, or from those salified with an inorganic acid such as, for example, hydrochloric acid and sulphuric acid, with the proviso that they give a visually clear solution at a weight concentration of 1% in water.

Among the chemically modified chitosans which may be mentioned, in particular, are the product sold under the name N,O-carboxymethylchitosan by the company Chitogenics Ltd, the N-carboxybutylchitosan sold under the trade names CHITOLAM NB 101 or EVALSAN by the company Chito Bios, the N-succinylchitosan sold by the company Chimex under the name MEXOMERE PAD, or sold by the company Francechitine under the name KITINAMI, or sold by the company Katakura Chikkarin under the name SUCCINYL CHITOSAN, and the N-succinylcarboxymethylchitosan sold under the name CHITOSOLLEN by the company Ikeda.

The salified or modified chitosan(s) of formula (I) used in the ready-to-use dye composition according to the invention preferably represent(s) from 0.01 to 20% by weight approximately relative to the total weight of the ready-to-use dye composition, and even more preferably from 0.1 to 5% by weight approximately relative to this weight.

The 2-electron oxidoreductase(s) used in the ready-to-use dye composition in accordance with the invention, in the presence of a donor for the enzyme(s), can be chosen, in particular, from pyranose oxidases, glucose oxidases, glycerol oxidases, lactate oxidases, pyruvate oxidases, uricases, choline oxidases, sarcosine oxidases, bilirubin oxidases and amino acid oxidases.

According to the invention, the 2-electron oxidoreductase is preferably chosen from uricases of animal, microbiological or biotechnological origin.

Particular examples include the uricase extracted from boar's liver, the uricase from Arthrobacter globiformis and the uricase from Aspergillus flavus.

The 2-electron oxidoreductase(s) can be used in pure crystalline form or in a dilute form in an inert diluent for the 2-electron oxidoreductase.

The 2-electron oxidoreductase(s) according to the invention preferably represent(s) from 0.01 to 20% by weight approximately relative to the total weight of the composition, and even more preferably from 0.1 to 5% by weight approximately relative to this weight.

The amount of enzyme can also be defined as a function of its activity.

The enzymatic activity of the 2-electron oxidoreductases according to the invention can be defined from the oxidation of the donor under aerobic conditions.

One U unit corresponds to the amount of enzyme leading to the generation of one $\mu$mol of $H_2O_2$ per minute at a pH of 8.5 and at a temperature of 25° C. Preferably, the amount of 2-electron oxidoreductase according to the invention is between 10 and $10^8$ U units approximately per 100 g of dye composition.

According to the invention, the term "donor" means the various substrates also required for the functioning of the 2-electron oxidoreductase(s).

The nature of the donor (or substrate) for the enzyme varies as a function of the nature of the 2-electron oxidoreductase used. For example, donors for the pyranose oxidases include D-glucose, L-sorbose and D-xylose; a donor for the glucose oxidases that may be mentioned is D-glucose; donors for the glycerol oxidases include glycerol and dihydroxyacetone; donors for the lactate oxidases include lactic acid and its salts; donors for the pyruvate oxidases include pyruvic acid and its salts; donors for the uricases include uric acid and its salts; donors for the choline oxidases include choline and its addition salts with an acid, such as choline hydrochloride and betaine aldehyde; donors for the sarcosine oxidases include sarcosine, N-methyl-L-leucine, N-methyl-D,L-alanine and N-methyl-D,L-valine; and, finally, a donor for the bilirubin oxidases that may be mentioned is bilirubin.

The donor(s) (or substrates) used in accordance with the invention preferably represent(s) from 0.01 to 20% by weight approximately relative to the total weight of the composition in accordance with the invention, and even more preferably from 0.1 to 5% approximately relative to this weight.

The 4-electron oxidoreductase(s) used in the ready-to-use dye composition in accordance with the invention can be chosen, in particular, from laccases, tyrosinases, catechol oxidases and polyphenol oxidases.

According to one specific and preferred embodiment of the invention, the 4-electron oxidoreductase(s) is(are) chosen from laccases.

These laccases can be chosen, in particular, from laccases of plant origin, of animal origin, of fungal origin, e.g., yeasts, molds and fungi, or of bacterial origin, the organisms of origin possibly being mono- or multicellular. The laccases can also be obtained by biotechnology.

Examples of the laccases of plant origin that can be used according to the invention include the laccases produced by plants that carry out chlorophyll synthesis, such as those mentioned in French patent application FR-A-2 694 018, the disclosure of which is incorporated herein by reference.

Particular examples include the laccases present in extracts of Anacardiacea plants such as, for example, extracts of *Magnifera indica, Schinus molle* or *Pleiogynium timoriense*; extracts of Podocarpacea plants; *Rosmarinus off.; Solanum tuberosum*; Iris sp.; Coffea sp.; *Daucus carrota; Vinca minor; Persea americana; Catharanthus roseus*; Musa sp.; *Malus pumila; Gingko biloba; Monotropa hypopithys* (Indian pipe), Aesculus sp.; *Acer pseudoplatanus; Prunus persica* and *Pistacia palaestina*.

Examples of the laccases of fungal origin, optionally obtained by biotechnology, that can be used according to the invention include the laccase(s) obtained from *Polyporus versicolor*, from *Rhizoctonia praticola* and from *Rhus vernicifera* as described, for example, in French patent application FR-A-2 112 549 and European patent application EP-A-504 005, the disclosures of each of which are incorporated herein by reference; the laccases described in International patent applications WO 95/07988, WO 95/33836, WO 95/33837, WO 96/00290, WO 97/19998 and WO 97/19999, the disclosures of each of which are incorporated herein by reference, such as, for example, the laccase(s) obtained from Scytalidium, from *Polyporus pinsitus*, from *Myceliophthora thermophila*, from *Rhizoctonia solani*, from *Pyricularia orizae*, and variants thereof. Mention may also be made of the laccase(s) obtained from *Trametes versicolor*, from *Fomes fomentarius*, from *Chaetomium thermophile*, from *Neurospora crassa*, from *Colorius versicol*, from *Botrytis cinerea*, from *Rigidoporus lignosus*, from *Phellinus noxius*, from *Pleurotus ostreatus*, from *Aspergillus nidulans*, from *Podospora anserina*, from *Agaricus bisporus*, from *Ganoderma lucidum*, from *Glomerella cingulata*, from *Lactarius piperatus*, from *Russula delica*, from *Heterobasidion annosum*, from *Thelephora terrestris*, from *Cladosporium cladosporioides*, from *Cerrena unicolor*, from *Coriolus hirsutus*, from *Ceriporiopsis subvermispora*, from *Coprinus cinereus*, from *Panaeolus papilionaceus*, from *Panaeolus sphinctrinus*, from *Schizophyllum commune*, from *Dichomitius squalens*, and from variants thereof.

Laccases of fungal origin, optionally obtained by biotechnology, will more preferably be chosen.

The enzymatic activity of the laccases used according to the invention and having syringaldazine among their substrates can be defined by the oxidation of syringaldazine under aerobic conditions. One Lacu unit corresponds to the amount of enzyme that catalyzes the conversion of 1 mmol of syringaldazine per minute at a pH of 5.5 and at a temperature of 30° C. One U unit corresponds to the amount of enzyme that produces an absorbance delta of 0.001 per minute at a wavelength of 530 nm, using syringaldazine as substrate, at 30° C. and at a pH of 6.5. The enzymatic activity of the laccases used according to the invention can also be defined by the oxidation of para-phenylenediamine. One ulac unit corresponds to the amount of enzyme that produces an absorbance delta of 0.001 per minute at a wavelength of 496.5 nm, using para-phenylenediamine as substrate (64 mM), at 30° C. and at a pH of 5.

In general, the 4-electron oxidoreductase(s) according to the invention preferably represent(s) from 0.01 to 20% by weight approximately relative to the total weight of the ready-to-use dye composition, and even more preferably from 0.1 to 5% by weight approximately relative to this weight.

In particular, and when one or more laccases are used, the amount of laccase(s) present in the ready-to-use dye composition according to the invention will vary as a function of the nature of the laccase(s) used. Preferably, the amount of laccase(s) is between 0.5 and 2000 Lacu approximately, i.e., between 10,000 and $40 \times 10^6$ U units approximately or alternatively between 20 and $20 \times 10^6$ ulac units per 100 g of ready-to-use dye composition.

The oxidation dye(s) used in the ready-to-use dye composition according to the invention can be chosen, in particular, from oxidation bases and/or couplers.

The oxidation bases are, in particular, para-phenylenediamines, double bases, para-aminophenols and heterocyclic bases.

Examples of para-phenylenediamines include those of formula (II) below, and the acid addition salts thereof:

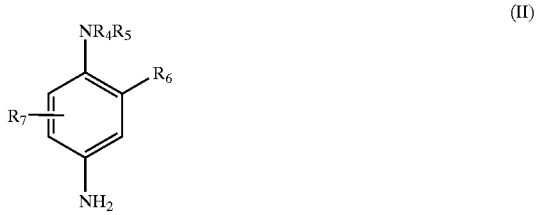

(II)

in which:

$R_4$ and $R_5$, which are identical or different, are chosen from a hydrogen atom, a $C_1$–$C_4$ alkyl radical and a $C_1$–$C_4$ monohydroxyalkyl radical;

$R_6$ is chosen from a hydrogen atom, a halogenatom, a $C_1$–$C_4$ alkyl radical and a $C_1$–$C_4$ monohydroxyalkyl radical;

$R_7$ is chosen from a hydrogen atom and a $C_1$–$C_4$ alkyl radical.

Particular examples of the para-phenylenediamines of formula (II) above include: para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-b-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine and N-ethyl-N-(β-hydroxyethyl)-para-phenylenediamine, and the acid addition salts thereof.

Particular examples of the double bases that can be used as oxidation base in the ready-to-use dye composition according to the invention include compounds comprising at least two aromatic nuclei on which are borne several amino and/or hydroxyl groups.

More particular examples of the double bases include the compounds of formula (III) below, and the acid addition salts thereof.

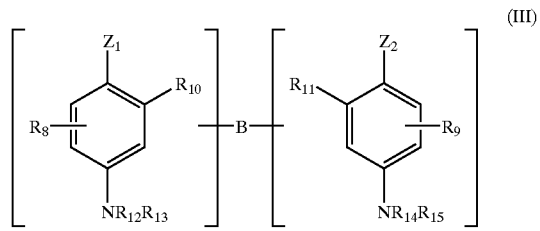

(III)

in which:

$Z_1$ and $Z_2$, which are identical or different, are chosen from a hydroxyl radical and an —$NH_2$ radical which can be substituted with a $C_1$–$C_4$ alkyl radical or with a linker arm B;

the linker arm B is chosen from a linear or branched alkylene chain containing from 1 to 14 carbon atoms, that can be interrupted or end with one or more nitrogenous groups and/or with one or more hetero atoms such as oxygen, sulphur or nitrogen atoms, and optionally substituted with one or more hydroxyl or $C_1$–$C_6$ alkoxy radicals;

$R_8$ and $R_9$ are chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical and a linker arm B;

$R_{10}$, $R_{11}$, $R_{12}$, $R_{13}$, $R_{14}$ and $R_{15}$, which are identical or different, are chosen from a hydrogen atom, a linker arm B and a $C_1$–$C_4$ alkyl radical;

with the proviso that the compounds of formula (III) comprise only one linker arm B per molecule.

Particular examples of the nitrogenous groups of formula (III) above include amino, mono($C_1$–$C_4$)alkylamino, di($C_1$–$C_4$)alkylamino, tri($C_1$–$C_4$)alkylamino, monohydroxy ($C_1$–$C_4$)alkylamino, imidazolinium and ammonium radicals.

More particular examples of the double bases of formula (III) above include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl) tetramethylenediamine, N,N'-bis(4-methylaminophenyl) tetramethylene-diamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

Among these double bases of formula (III), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the acid addition salts thereof, are particularly preferred.

Particular examples of the para-aminophenols that can be used as oxidation base in the ready-to-use dye composition according to the invention include those of formula (IV) below, and the acid addition salts thereof:

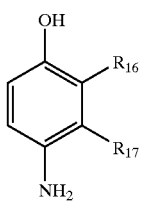

(IV)

in which:

R$_{16}$ and R$_{17}$, which are identical or different, are chosen from a hydrogen atom, a halogen atom, a C$_1$–C$_4$ alkyl radical, a C$_1$–C$_4$ monohydroxyalkyl radical, a (C$_1$–C$_4$) alkoxy(C$_1$–C$_4$)alkyl radical, a C$_1$–C$_4$ aminoalkyl radical and a monohydroxy(C$_1$–C$_4$)alkylamino(C$_1$–C$_4$) alkyl radical, with the proviso that at least one of the radicals R$_{16}$ and R$_{17}$ is a hydrogen atom.

More particular examples of the para-aminophenols of formula (IV) described above include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxy-ethylaminomethyl)phenol and 4-amino-2-fluorophenol, and the acid addition salts thereof.

Particular examples of the heterocyclic bases that can be used as oxidation base in the ready-to-use dye composition according to the invention include pyridine derivatives, pyrimidine derivatives and pyrazole derivatives, and the acid addition salts thereof.

Particular examples of the pyridine derivatives include the compounds described, for example, in British patents GB 1 026 978 and GB 1 153 196, the disclosures of each of which are incorporated herein by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Particular examples of the pyrimidine derivatives include the compounds described, for example, in German patent DE 2 359 399 or Japanese patents JP 88-169 571 and JP 91-10659 or International patent application WO 96/15765, the disclosures of each of which are incorporated herein by reference, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolo-pyrimidine derivatives such as those mentioned in French patent application FR-A-2 750 048, the disclosure of which is incorporated herein by reference, and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine, and the addition salts thereof and the tautomeric forms thereof, when a tautomeric equilibrium exists, and the acid addition salts thereof.

Particular examples of the pyrazole derivatives include the compounds described in German patents DE 3 843 892 and DE 4 133 957 and International patent applications WO 94/08969, WO 94/08970, French patent application FR-A-2 733 749 and German patent application DE 195 43 988, the disclosures of each of which are incorporated herein by reference, such as 4,5-diamino-1-methylpyrazole, 3,4-diaminopyrazole, 4,5-diamino-1-(4'-chlorobenzyl) pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the acid addition salts thereof.

The couplers are, in particular, meta-aminophenols, meta-phenylenediamines, meta-diphenols, heterocyclic couplers such as, for example, indole derivatives, indoline derivatives, sesamol and its derivatives, pyridine derivatives, pyrazolotriazole derivatives, and pyrazolones, and the acid addition salts thereof.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the acid addition salts thereof.

In general, the addition salts with an acid that can be used in the context of the dye compositions of the invention (oxidation bases and couplers) are chosen, in particular, from the hydrochlorides, hydrobromides, sulphates, tartrates, lactates and acetates.

According to the invention, the oxidation dye(s) preferably represent(s) from 0.001 to 20% by weight approximately relative to the total weight of the ready-to-use dye composition, and even more preferably from 0.01 to 10% by weight approximately relative to this weight.

According to one preferred embodiment, the ready-to-use dye composition according to the invention can also contain one or more direct dyes, in particular, to modify the shades by enriching them with glints.

The medium suitable for dyeing or support for the ready-to-use dye composition in accordance with the invention generally comprises water or a mixture of water and at least one organic solvent to dissolve the compounds not sufficiently soluble in water. Examples of organic solvents include C$_1$–C$_4$ alkanols, such as ethanol and isopropanol; glycerol; glycols and glycol ethers, such as 2-butoxyethanol, propylene glycol, propylene glycol monomethyl ether, diethylene glycol monoethyl ether and monomethyl ether; as well as aromatic alcohols, such as benzyl alcohol or phenoxy ethanol, similar products and mixtures thereof.

The solvents can be present in proportions preferably ranging from 1 to 40% by weight approximately relative to the total weight of the ready-to-use dye composition, and even more preferably from 5 to 30% by weight approximately.

The pH of the ready-to-use composition according to the invention is chosen such that the enzymatic activity of the 2-electron or 4-electron oxidoreductase is sufficient. It generally ranges from 3 to 11 approximately, and preferably from 4 to 9 approximately. It can be adjusted to the desired value using acidifying or basifying agents usually used in the dyeing of keratin fibers.

Examples of the acidifying agents include inorganic or organic acids, such as hydrochloric acid, orthophosphoric acid, sulphuric acid, carboxylic acids, such as acetic acid, tartaric acid, citric acid or lactic acid, and sulphonic acids.

Examples of basifying agents include aqueous ammonia, alkaline carbonates, alkanolamines such as mono-, di- and triethanolamines, 2-methyl-2-amino-1-propanol and derivatives thereof, sodium hydroxide, potassium hydroxide and the compounds of formula (V) below:

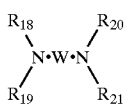

(V)

in which W is a propylene residue optionally substituted with a hydroxyl group or a $C_1$–$C_4$ alkyl radical; $R_{18}$, $R_{19}$, $R_{20}$ and $R_{21}$, which may be identical or different, represent a hydrogen atom, a $C_1$–$C_4$ alkyl radical or a $C_1$–$C_4$ hydroxyalkyl radical.

The ready-to-use dye composition according to the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrating agents, sequestering agents, fragrances, buffers, dispersants, conditioners, such as, for example, volatile or non-volatile, modified or unmodified silicones, film-forming agents, ceramides, preserving agents and opacifiers.

Needless to say, a person skilled in the art will take care to select this or these optional additional compound(s) such that the advantageous properties intrinsically associated with the ready-to-use dye composition according to the invention are not, or are not substantially, adversely affected by the addition(s) envisaged.

The ready-to-use dye composition according to the invention can be in various forms, such as in the form of liquids, creams or gels, optionally pressurized, or in any other form suitable for dyeing keratin fibers, and, in particular, human hair. In the case where the oxidation dyes and the 2-electron or 4-electron oxidoreductase(s) are packaged in the same ready-to-use composition, the packaged composition should be free of oxygen gas, so as to avoid any premature oxidation of the oxidation dye(s).

A subject of the invention is also a process for dyeing keratin fibers, and, in particular, human keratin fibers, such as the hair, using the ready-to-use dye composition as defined above.

According to this process, at least one ready-to-use dye composition as defined above is applied to the fibers, at an application temperature of between room temperature and 80° C., for a period sufficient to develop the desired coloration. Preferably, the fibers are then rinsed, optionally washed with shampoo, and then dried.

The application temperature preferably ranges from room temperature to 60° C. and even more preferably from 35° C. to 50° C.

The time sufficient to develop the coloration on the keratin fibers generally ranges from 1 to 60 minutes and even more specifically from 5 to 30 minutes.

According to one specific embodiment of the invention, the process comprises a preliminary step which comprises separately storing a composition (A) comprising, in a medium suitable for dyeing, at least one oxidation dye, i.e., base and/or coupler, as defined above, and a composition (B) comprising, in a medium suitable for dyeing, at least one enzyme of 2-electron or 4-electron oxidoreductase type, wherein the composition (A) and/or the composition (B) comprises at least one salified or chemically modified chitosan as defined above, and then in mixing them together at the time of use, after which this mixture is applied to the keratin fibers.

Another subject of the invention is a multi-compartment dyeing device or dyeing "kit" or any other multi-compartment packaging system with at least two compartments, wherein one compartment comprises a composition (A), as defined above, and another compartment comprises a composition (B), as defined above. These devices can be equipped with a means for applying the desired mixture to the hair, such as the devices described in French patent FR-2 586 913 in the name of L'Oréal, the disclosure of which is incorporated herein by reference.

The present invention is further illustrated by the following examples which are designed to teach those of ordinary skill in the art how to practice the invention. The following examples are merely illustrative of the invention and should not be construed as limiting the invention as claimed.

EXAMPLE 1

A dye composition B according to the invention containing an N,O-carboxymethylchitosan as thickener was compared with a composition A of the prior art containing as thickener a methacrylic acid/ethyl acrylate/stearyl methacrylate oxyethylenated terpolymer as an aqueous 30% dispersion (ACULYN 22 from Rohm & Haas). See the table below.

Composition A (not of the invention)

| | |
|---|---|
| para-Toluenediamine | 0.122 g |
| 3,6-Dimethyl-1H-pyrazolo[5,1-c][1,2,4]triazole | 0.136 g |
| ACULYN 22 (Rohm & Haas) | 0.75 g AM* |
| Laccase obtained from Trametes versicolor | 10 × 10⁶ U units |
| pH agent | qs pH 7 |
| Demineralized water qs | 100 g |

*denotes Active Material

Composition B (invention)

| | |
|---|---|
| para-Toluenediamine | 0.122 g |
| 3,6-Dimethyl-1H-pyrazolo[5,1-c][1,2,4]triazole | 0.136 g |
| N,O-Carboxymethylchitosan - Chitogenics Ltd | 0.75 g AM* |
| Laccase obtained from Trametes versicolor | 10 × 10⁶ U units |
| pH agent | qs pH 7 |
| Demineralized water qs | 100 g |

Each of these compositions was applied to locks of natural gray hair containing 90% white hairs, for 30 minutes at 40° C. After the exposure time, the locks of hair were rinsed, washed with a shampoo and then dried.

The color was then measured using a Minolta CM2002 colorimeter in the L*a*b* system. In the L*a*b* system, the 3 parameters denote, respectively, the intensity (L*), the shade (a*) and the saturation (b*).

According to this system, the higher the value of L, the lighter or less intense the color. Conversely, the lower the value of L, the darker or more intense the color.

a* and b* indicate two color axes: a* indicates the green/red color axis and b* indicates the blue/yellow color axis. Values close to zero for a* and b* correspond to gray shades.

The rise in the coloration ΔE can be calculated by applying the following equation:

$$\Delta E = \sqrt{(L^*-L_o^*)^2 + (a^*-a_o^*)^2 + (b^*-b_o^*)^2}$$

In this equation, ΔE represents the difference in color between two locks (in the present case the rise in the coloration), L*, a* and b* represent, respectively, the intensity, shade and saturation of the dyed lock, $L_o^*$, $a_o^*$ and $b_o^*$ representing, respectively, the intensity, shade and saturation of the undyed control lock.

The higher the value of ΔE, the greater the difference in color between the two locks, and, in the present case, the greater the rise in the coloration and thus the stronger the dyeing effect.

The results are collated in Table (I) below.

TABLE (I)

| Composition | L* | a* | b* | Rise in the coloration(ΔE) |
|---|---|---|---|---|
| A (comparative) | 36.58 | 21.28 | 5.45 | 29.75 |
| B (inventive) | 33.50 | 24.28 | 5.55 | 32.57 |
| Control (not colored) | 57.52 | 1.07 | 11.64 | — |

These results demonstrated that the dye containing N,O-carboxymethylchitosan (according to the invention) was more intense than that containing ACULYN 22 (not of the invention).

EXAMPLE 2

The conservation of the enzymatic activity of a laccase in two compositions was compared. Comparative composition A contained the laccase in a medium containing a thickener of the prior art, ACULYN 22. Inventive composition B contained the laccase in a medium according to the present invention, i.e., containing an N,O-carboxymethylchitosan. See the table below.

Composition A (not of the invention)

| ACULYN 22 (Rohm & Haas) | 0.75 g AM* |
|---|---|
| Laccase obtained from Trametes versicolor | 10 × 10⁶ U units |
| pH agent | qs pH 7 |
| Demineralized water qs | 100 g |

*denotes Active Material

Composition B (invention)

| N,O-carboxymethylchitosan - Chitogenics Ltd | 0.75 g AM* |
|---|---|
| Laccase SP809 - Novo Nordisk | 10 × 10⁶ U units |
| pH agent | qs pH 7 |
| Demineralized water qs | 100 g |

The results are collated on the curve in Table (II) below:

TABLE (II)

CONSERVATION OF LACCASE OBTAINED FROM TRAMETES VERSICOLOR IN A GEL OF N,O-CARBOXYMETHYLCHITOSAN COMPARED WITH A GEL COTAINING ACULYN 22 (room temperature)

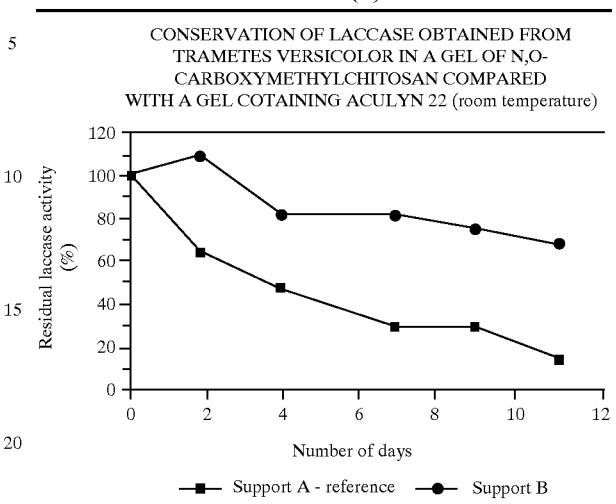

—■— Support A - reference   —●— Support B

These results demonstrated that laccase was conserved more effectively in a medium containing N,O-carboxymethylcellulose (a medium according to the invention with support B).

The foregoing written description relates to various embodiments of the present invention. Numerous changes and modifications may be made therein without departing from the spirit and scope of the invention as defined in the following claims.

What is claimed is:

1. A ready-to-use composition for the oxidation dyeing of keratin fibers, comprising:
   at least one oxidation dye,
   at least one 2-electron or 4-electron oxidoreductase enzyme, and
   at least one chitosan chosen from
      at least one chitosan salified with an organic or inorganic acid, wherein said at least one chitosan allows a visually clear solution to be obtained at a concentration of 1% in water, and
      at least one chemically modified chitosan,
   wherein said at least one chitosan comprises at least one unit of formula (I):

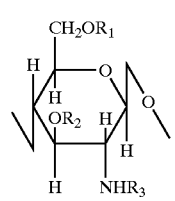

(I)

in which,
$R_1$ and $R_2$, which are identical or different, are chosen from a hydrogen atom and a radical —XCOOM,
$R_3$ is chosen from a hydrogen atom, a —COCH$_3$ radical and a radical —CO—X—COOM,
X is chosen from a $C_1$–$C_8$ alkylene radical, which is optionally branched, or substituted with at least one hydroxyl, halogen or epoxy group,
M is chosen from a hydrogen atom and a cation chosen from alkali metals, alkaline-earth metals, ammonium, an organic amine and an organic alkanolamine, with the proviso that at least one of the units of formula (I) contains a radical —XCOOM or a radical —CO—X—COOM.

2. A composition according to claim 1, wherein said keratin fibers are human keratin fibers.

3. A composition according to claim 2, wherein said human keratin fibers are human hair.

4. A composition according to claim 1, wherein said composition further comprises a medium suitable for dyeing.

5. A composition according to claim 1, in which said at least one chitosan salified with an organic acid is a chitosan pyrrolidonecarboxylate.

6. A composition according to claim 1, wherein said at least one chemically modified chitosan of formula (I) is chosen from an N,O-carboxymethylchitosan, an N-carboxybutylchitosan, an N-succinylchitosan and an N-succinylcarboxymethylchitosan.

7. A composition according to claim 6, wherein said at least one chemically modified chitosan of formula (I) is N,O-carboxymethylchitosan.

8. A composition according to claim 1, wherein said at least one salified or modified chitosan of formula (I) is present in an amount ranging from 0.01 to 20% by weight relative to the total weight of said composition.

9. A composition according to claim 8, wherein said at least one salified or modified chitosan of formula (I) is present in an amount ranging from 0.1 to 5% by weight relative to the total weight of said composition.

10. A composition according to claim 1, wherein said at least one 2-electron oxidoreductase enzyme is chosen from pyranose oxidases, glucose oxidases, glycerol oxidases, lactate oxidases, pyruvate oxidases, uricases, choline oxidases, sarcosine oxidases, bilirubin oxidases and amino acid oxidases, and further wherein said at least one enzyme is used with a donor for said at least one enzyme.

11. A composition according to claim 1, wherein said at least one 4-electron oxidoreductase enzyme is chosen from laccases, tyrosinases, catechol oxidases and polyphenol oxidases.

12. A composition according to claim 11, wherein said laccases are chosen from laccases of plant origin, of animal origin, of fungal origin and of bacterial origin and from laccases obtained by biotechnology.

13. A composition according to claim 12, wherein said laccases of plant origin are chosen from laccases present in extracts of Anacardiacea plants; of Podocarpacea plants; of *Rosmarinus off.*; of *Solanum tuberosum*; of Iris sp.; of *Coffea* sp.; of *Daucus carrota*; of *Vinca minor*; of *Persea americana*; of *Catharanthus roseus*; of *Musa* sp.; of *Malus pumila*; of *Gingko biloba*; of *Monotropa hypopithys*, of *Aesculus* sp.; of *Acer pseudoplatanus*; of *Prunus persica* and of *Pistacia palaestina*.

14. A composition according to claim 12, wherein said laccases are of fungal origin or obtained by biotechnology.

15. A composition according to claim 14, wherein said laccases are chosen from laccases obtained from *Polyporus versicolor*, from *Rhizoctonia praticola*, from *Rhus vernicifera*, from Scytalidium, from *Polyporus pinsitus*, from *Myceliophtora thermophila*, from *Rhizoctonia solani*, from *Pyricularia orizae*, from *Trametes versicolor*, from *Fomes fomentarius*, from *Chaetomium thermophile*, from *Neurospora crassa*, from *Colorius versicol*, from *Botrytis cinerea*, from *Rigidoporus lignosus*, from *Phellinus noxius*, from *Pleurotus ostreatus*, from *Aspergillus nidulans*, from *Podospora anserina*, from *Agaricus bisporus*, from *Ganoderma lucidum*, from *Glomerella cingulata*, from *Lactarius piperatus*, from *Russula delica*, from *Heterobasidion annosum*, from *Thelephora terrestris*, from *Cladosporium cladosporioides*, from *Cerrena unicolor*, from *Coriolus hirsutus*, from *Ceriporiopsis subvermispora*, from *Coprinus cinereus*, from *Panaeolus papilionaceus*, from *Panaeolus sphinctrinus*, from *Schizophyllum commune*, from *Dichomitius squalens*, and from variants thereof.

16. A composition according to claim 1, wherein said at least one 2-electron or 4-electron oxidoreductase enzyme is present in an amount ranging from 0.01 to 20% by weight relative to the total weight of said composition.

17. A composition according to claim 16, wherein said at least one 2-electron or 4-electron oxidoreductase enzyme is present in an amount ranging from 0.1 to 5% by weight relative to the total weight of said composition.

18. A composition according to claim 1, wherein said at least one oxidation dye is chosen from oxidation bases and couplers.

19. A composition according to claim 18, wherein said oxidation bases are chosen from para-phenylenediamines, double bases, para-aminophenols, heterocyclic bases, and acid addition salts thereof.

20. A composition according to claim 19, wherein said para-phenylenediamines are chosen from those of formula (II), and acid addition salts thereof:

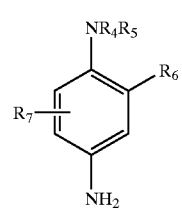

(II)

in which:

$R_4$ and $R_5$, which are identical or different, are chosen from a hydrogen atom, a $C_1$–$C_4$ alkyl radical and a $C_1$–$C_4$ monohydroxyalkyl radical;

$R_6$ is chosen from a hydrogen atom, a halogen atom, a $C_1$–$C_4$ alkyl radical and a $C_1$–$C_4$ monohydroxyalkyl radical; and $R_7$ is chosen from a hydrogen atom and a $C_1$–$C_4$ alkyl radical.

21. A composition according to claim 20, wherein said para-phenylenediamines of formula (II) are chosen from:

para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, and acid addition salts thereof.

22. A composition according to claim 19, wherein said double bases are chosen from compounds of formula (III), and acid addition salts thereof:

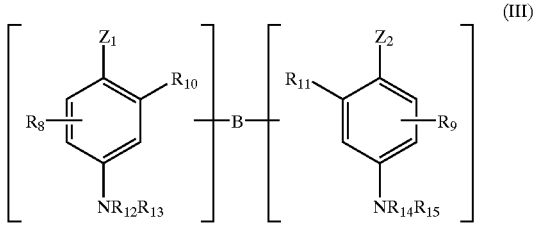

in which:
- $Z_1$ and $Z_2$, which are identical or different, are chosen from a hydroxyl and an —$NH_2$ radical which is optionally substituted with a $C_1$–$C_4$ alkyl radical or with a linker arm B;
- linker arm B is chosen from a linear or branched alkylene chain containing from 1 to 14 carbon atoms, which is optionally interrupted or optionally ends with at least one of one or more nitrogenous groups and one or more hetero atoms, and is optionally substituted with one or more hydroxyl or $C_1$–$C_6$ alkoxy radicals;
- $R_8$ and $R_9$ are chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical and a linker arm B;
- $R_{10}$, $R_{11}$, $R_{12}$, $R_{13}$, $R_{14}$ and $R_{15}$, which are identical or different, are chosen from a hydrogen atom, a linker arm B and a $C_1$–$C_4$ alkyl radical;

with the proviso that said compounds of formula (III) comprise only one linker arm B per molecule.

23. A composition according to claim 22, wherein in said linker arm B, said heteroatoms are chosen from oxygen, sulfur and nitrogen atoms.

24. A composition according to claim 22, wherein said double bases of formula (III) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylene-diamine, N,N'-bis(ethyly)-N,N'-bis(4'-amino-3'-methylphenyl)ethylenediamine, 1,8-bis(2,5-diaminophenoxy)-3,5-dioxaoctane, and acid addition salts thereof.

25. A composition according to claim 19, wherein said para-aminophenols are chosen from those of formula (IV), and acid addition salts thereof:

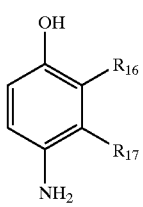

in which:
- $R_{16}$ and $R_{17}$, which are identical or different, are chosen from a hydrogen atom, a halogen atom, a $C_1$–$C_4$ alkyl radical, a $C_1$–$C_4$ monohydroxyalkyl radical, a ($C_1$–$C_4$) alkoxy($C_1$–$C_4$)alkyl radical, a $C_1$–$C_4$ aminoalkyl radical and a monohydroxy($C_1$–$C_4$)alkylamino($C_1$–$C_4$) alkyl radical, with the proviso that at least one of the radicals $R_{16}$ and $R_{17}$ is a hydrogen atom.

26. A composition according to claim 25, wherein said para-aminophenols of formula (IV) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

27. A composition according to claim 19, wherein said heterocyclic bases are chosen from pyridine derivatives, pyrimidine derivatives, pyrazole derivatives, and acid addition salts thereof.

28. A composition according to claim 18, wherein said couplers are chosen from meta-aminophenols, meta-phenylenediamines, meta-diphenols, heterocyclic couplers, and acid addition salts thereof.

29. A composition according to claim 28, wherein said couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and acid addition salts thereof.

30. A composition according to claim 1, wherein said at least one oxidation dye is present in an amount ranging from 0.001 to 20% by weight relative to the total weight of said composition.

31. A composition according to claim 30, wherein said at least one oxidation dye is present in an amount ranging from 0.01 to 10% by weight relative to the total weight of said composition.

32. A composition according to claim 1, further comprising at least one direct dye.

33. A composition according to claim 1, wherein said composition has a pH ranging from 3 to 11.

34. A composition according to claim 4, wherein said medium suitable for dyeing is water or a mixture of water and at least one organic solvent.

35. A process for the oxidation dyeing of keratin fibers comprising:

applying to said keratin fibers at least one ready-to-use dye composition at an application temperature ranging from room temperature to 80° C., wherein said at least one ready-to-use composition comprises:
- at least one oxidation dye,
- at least one 2-electron or 4-electron oxidoreductase enzyme, and
- at least one chitosan chosen from
  - at least one chitosan salified with an organic or inorganic acid, wherein said at least one chitosan allows a visually clear solution to be obtained at a concentration of 1% in water, and
  - and at least one chemically modified chitosan,
- wherein said at least one chitosan comprises at least one unit of formula (I):

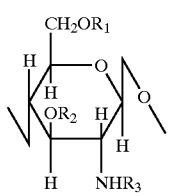

(I)

in which,
R$_1$ and R$_2$, which are identical or different, are chosen from a hydrogen atom and a radical —XCOOM, R$_3$ is chosen from a hydrogen atom, a —COCH$_3$ radical and a radical —CO—X—COOM, X is chosen from a C$_1$–C$_8$ alkylene radical, which is optionally branched, or substituted with at least one hydroxyl, halogen or epoxy group, M is chosen from a hydrogen atom and a cation chosen from alkali metals, alkaline-earth metals, ammonium, an organic amine and an organic alkanolamine, with the proviso that at least one of the units of formula (I) contains a radical —XCOOM or a radical —CO—X—COOM, and leaving said at least one ready-to-use composition on said keratin fibers for a period sufficient to develop a desired coloration.

36. A process according to claim 35, wherein said keratin fibers are human keratin fibers.

37. A process according to claim 36, wherein said human keratin fibers are human hair.

38. A process according to claim 35, wherein said application temperature ranges from room temperature to 50° C.

39. A process according to claim 35, wherein said period of time sufficient to develop the coloration ranges from 1 to 60 minutes.

40. A process according to claim 39, wherein said period of time sufficient to develop the coloration ranges from 5 to 30 minutes.

41. A process for the oxidation dyeing of keratin fibers comprising:

separately storing at least a first and a second composition, wherein said first composition comprises, in a medium suitable for dyeing, at least one oxidation dye, wherein said second composition comprises, in a medium suitable for dyeing, at least one 2-electron or 4-electron oxidoreductase enzyme, and wherein at least one of said first and said second separately stored compositions further comprises:
at least one chitosan chosen from
at least one chitosan salified with an organic or inorganic acid, wherein said at least one chitosan allows a visually clear solution to be obtained at a concentration of 1% in water, and
at least one chemically modified chitosan,
wherein said at least one chitosan comprises at least one unit of formula (I):

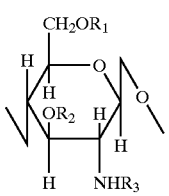

(I)

in which,
R$_1$ and R$_2$, which are identical or different, are chosen from a hydrogen atom and a radical —XCOOM, R$_3$ is chosen from a hydrogen atom, a —COCH$_3$ radical and a radical —CO—X—COOM, X is chosen from a C$_1$–C$_8$ alkylene radical, which is optionally branched, or substituted with at least one hydroxyl, halogen or epoxy group, M is chosen from a hydrogen atom and a cation chosen from alkali metals, alkaline-earth metals, ammonium, an organic amine and an organic alkanolamine, with the proviso that at least one of the units of formula (I) contains a radical —XCOOM or a radical —CO—X—COOM, and mixing said separately stored compositions to form a ready-to-use dye composition, applying said ready-to-use dye composition to said keratin fibers; and leaving said ready-to-use composition on said keratin fibers for a period sufficient to develop a desired coloration, wherein said separately stored compositions are mixed at or just prior to time of application of said ready-to-use dye composition to said keratin fibers.

42. A multi-compartment dyeing device, comprising at least a first and second compartment, wherein a first compartment comprises, in a medium suitable for dyeing, at least one oxidation dye, wherein a second compartment comprises, in a medium suitable for dyeing, at least one 2-electron or 4-electron oxidoreductase enzyme, and wherein at least compartment further comprises:
at least one chitosan chosen from
at least one chitosan salified with an organic or inorganic acid, wherein said at least one chitosan allows a visually clear solution to be obtained at a concentration of 1% in water, and
at least one chemically modified chitosan,
wherein said at least one chitosan comprises at least one unit of formula (I):

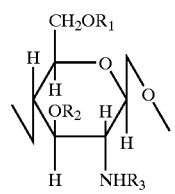

(I)

in which,
R$_1$ and R$_2$, which are identical or different, are chosen from a hydrogen atom and a radical —XCOOM, $R_3$ is chosen from a hydrogen atom, a —COCH$_3$ radical and a radical —CO—X—COOM, X is chosen from a $C_1$–$C_8$ alkylene radical, which is optionally branched, or substituted with at least one hydroxyl, halogen or epoxy group, M is chosen from a hydrogen atom and a cation chosen from alkali metals, alkaline-earth metals, ammonium, an organic amine and an organic alkanolamine, with the proviso that at least one of the units of formula (I) contains a radical —XCOOM or a radical —CO—X—COOM.

* * * * *

UNITED STATES PATENT AND TRADEMARK OFFICE
CERTIFICATE OF CORRECTION

PATENT NO. : 6,599,328 B1
DATED : July 29, 2003
INVENTOR(S) : Grégory Plos et al.

It is certified that error appears in the above-identified patent and that said Letters Patent is hereby corrected as shown below:

Column 15,
Lines 42-44, "N,N'-bis(ethyly)-N,N'-bis(4'-amino-3'-methylphenyl)ethylenediamine," should read -- N,N'-bis(ethyl)-N,N'-bis(4'-amino-3'-methylphenyl)ethylenediamine, --.

Signed and Sealed this

Second Day of March, 2004

JON W. DUDAS
*Acting Director of the United States Patent and Trademark Office*